(12) United States Patent
Royer

(10) Patent No.: US 11,832,540 B1
(45) Date of Patent: Dec. 5, 2023

(54) ROLLING SOIL PROBE

(71) Applicant: Jeffrey L. Royer, Neola, IA (US)

(72) Inventor: Jeffrey L. Royer, Neola, IA (US)

(*) Notice: Subject to any disclaimer, the term of this patent is extended or adjusted under 35 U.S.C. 154(b) by 600 days.

(21) Appl. No.: 17/089,171

(22) Filed: Nov. 4, 2020

(51) Int. Cl.
| | | |
|---|---|---|
| *A01B 35/28* | (2006.01) | |
| *G01N 1/08* | (2006.01) | |
| *B60D 1/14* | (2006.01) | |
| *B60P 3/00* | (2006.01) | |
| *B62D 49/00* | (2006.01) | |
| *A01B 76/00* | (2006.01) | |
| *A01B 79/00* | (2006.01) | |
| *A01B 35/16* | (2006.01) | |
| *A01B 35/32* | (2006.01) | |
| *A01B 29/06* | (2006.01) | |
| *G01N 33/24* | (2006.01) | |
| *B60D 1/00* | (2006.01) | |

(52) U.S. Cl.
CPC .............. *A01B 35/28* (2013.01); *A01B 29/06* (2013.01); *A01B 35/16* (2013.01); *A01B 35/32* (2013.01); *A01B 76/00* (2013.01); *A01B 79/00* (2013.01); *B60D 1/141* (2013.01); *B60P 3/00* (2013.01); *B62D 49/00* (2013.01); *G01N 1/08* (2013.01); *B60D 2001/008* (2013.01); *G01N 33/24* (2013.01); *G01N 2033/245* (2013.01)

(58) Field of Classification Search
CPC .... G01N 1/08; G01N 33/24; G01N 2033/245; A01B 29/06; A01B 35/16; A01B 35/28; A01B 35/32; A01B 76/00; A01B 79/00; B60D 1/141; B60D 2001/008
See application file for complete search history.

(56) References Cited

U.S. PATENT DOCUMENTS

| | | | | |
|---|---|---|---|---|
| RE30,901 E | * | 4/1982 | Boxrud | .............. G01N 1/08 73/864.45 |
| 6,766,865 B1 | * | 7/2004 | Dagel | ............... G01N 33/24 172/457 |
| 8,613,234 B1 | * | 12/2013 | Harrell | ................ G01N 1/08 73/864.41 |
| 9,200,492 B2 | | 12/2015 | McGraw | |
| 9,534,464 B1 | | 1/2017 | Kelley et al. | |
| 10,145,192 B1 | | 12/2018 | Kelley et al. | |
| 2010/0028080 A1 | * | 2/2010 | Wallace | .............. E02D 3/026 404/117 |

FOREIGN PATENT DOCUMENTS

CA 2975458 A1 * 2/2018 ............ A01B 29/04

* cited by examiner

*Primary Examiner* — Benjamin R Schmitt
(74) *Attorney, Agent, or Firm* — Ryan T. Grace; Advent, LLP

(57) ABSTRACT

A rolling soil probe which may be pulled by a tractor or a truck or mounted on a trailer. The rolling soil probe includes a rotatable square wheel having four sides, each of which has a soil probe extending outwardly therefrom.

20 Claims, 14 Drawing Sheets

ROLLING SOIL PROBE

BACKGROUND OF THE INVENTION

Field of the Invention

This invention relates to a soil probe and more particularly relates to a rolling soil probe for sampling soil. Even more particularly, this invention relates to a rolling soil probe having a rolling square wheel with a soil probe positioned on each of the four flat sides of the square wheel and which extend therefrom.

Description of the Related Art

Soil samplers or soil probes are commonly used to extract a soil core or plug from the ground for analysis. Many soil sampling devices have been previously provided with those devices ranging from hand-held probes to large soil sampling machines. Most of the soil sampling devices on the market are very expensive, difficult to use, difficult to maintain, and costly to repair, etc.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

A rolling soil probe is disclosed for pulling soil samples from the ground as the rolling soil probe is rolled over the ground to be sampled. In one embodiment, the rolling soil probe is mounted to the 3-point hitch at the rear end of a tractor. In a second embodiment, the rolling soil probe is mounted at the rear end of a truck. In a third embodiment, the rolling soil probe is mounted on a trailer.

In each of the embodiments, the rolling soil probe includes a frame means having a vertically disposed square wheel rotatably mounted therein about a horizontally disposed and transversely extending hub and spindle assembly. The square wheel includes a vertically disposed square plate having first, second, third and fourth side edges. The square plate is secured to the hub and spindle assembly for rotation therewith. Plates are secured to the first, second, third and fourth side edges of the square plate respectively. Each of the first, second, third and fourth support plates have a central opening formed therein. An elongated and hollow soil probe, having inner and outer ends, is secured to each of the first, second, third and fourth support plates so that the inner end of the said probe is in communication with the central opening of the respective support plate and so that the soil probe extends transversely outwardly from the respective support plate. Each of the soil probes has a hollow tip secured to the outer end thereof. Each of the tips have an opening outer end having a diameter which is less than the inner diameter of the body portion of the soil probe.

As the rolling soil probe is rolled along the ground, the lowermost soil probe punches into the ground at a right angle to the ground so that a soil sample is received within the soil probe. When the filled soil probe is at the upper end of the rolling soil probe, the soil sample within the soil probe, drops downwardly from the inner end of the soil probe into a soil sample collection container.

When the rolling soil probe is rolled along the ground, it is free floating and does not have any downward pressure exerted thereon by the hitches. The various hitches allow the rolling soil probe to be raised to a transport portion. The hitches do allow the rolling soil probe to pivot about a vertical axis so that the rolling soil probe may be pulled in a circular fashion.

It is therefore a principal object of the invention to provide an improved soil sampler probe apparatus.

A further object of the invention is to provide a rolling soil probe for obtaining soil samples.

A further object of the invention is to provide a rolling soil probe which includes a square wheel having four sides with each of the sides having a soil probe extending therefrom.

Yet another object of the invention is to provide a rolling soil probe which may be moved in a circular manner.

Yet another object of the invention is to provide a rolling soil probe which may be mounted on a trailer.

Still another object of the invention is to provide a soil probe including a hollow body portion having a tip at the outer end thereof which has an internal diameter which is less than the diameter of the hollow body portion of the soil probe.

Still another object of the invention is to provide a rolling soil probe which is economical of manufacture, durable in use and refined in appearance.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

Figure 15:
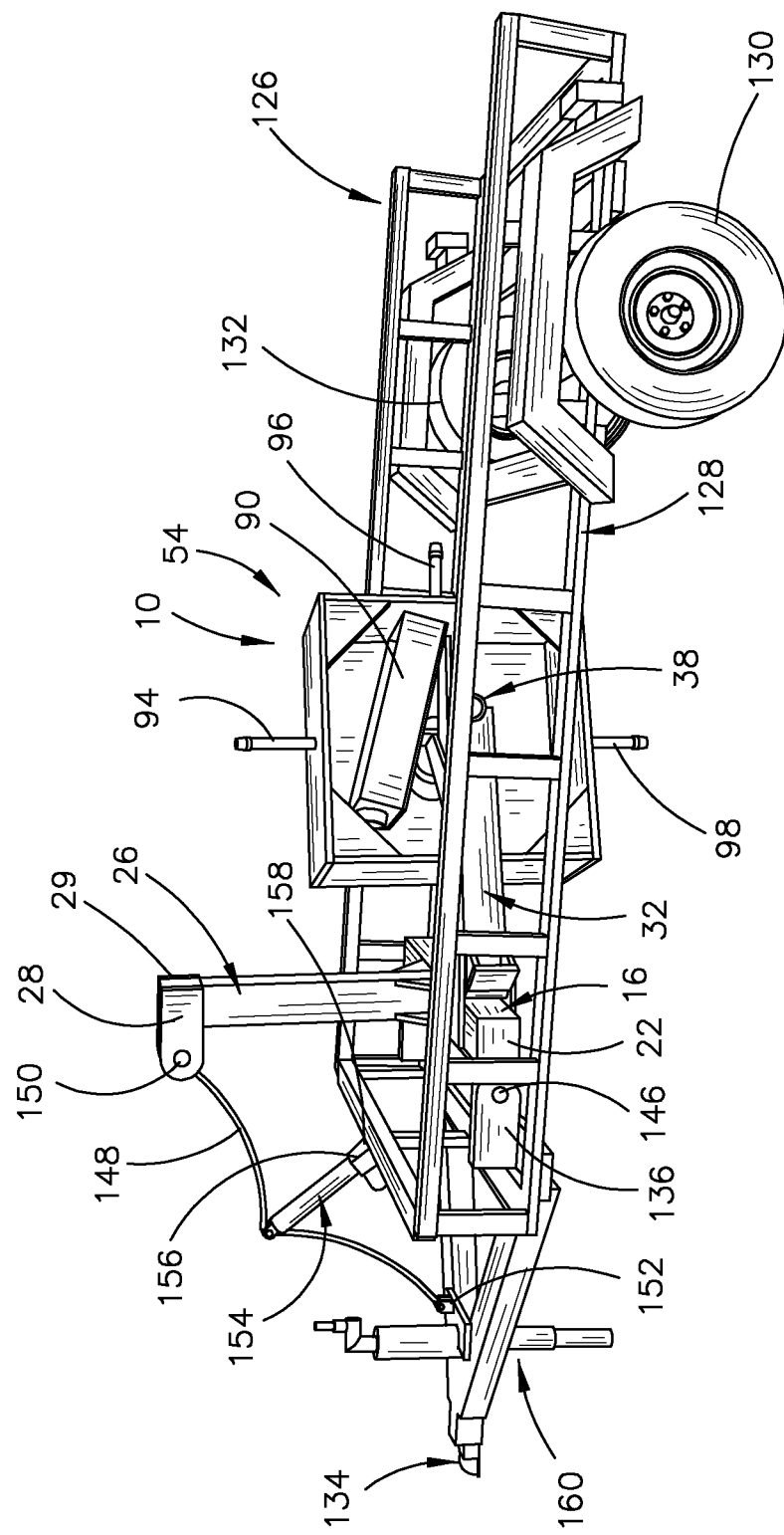
FIG. 15 is a side perspective view of the rolling soil probe assembly being mounted on a trailer.
Figure 16:
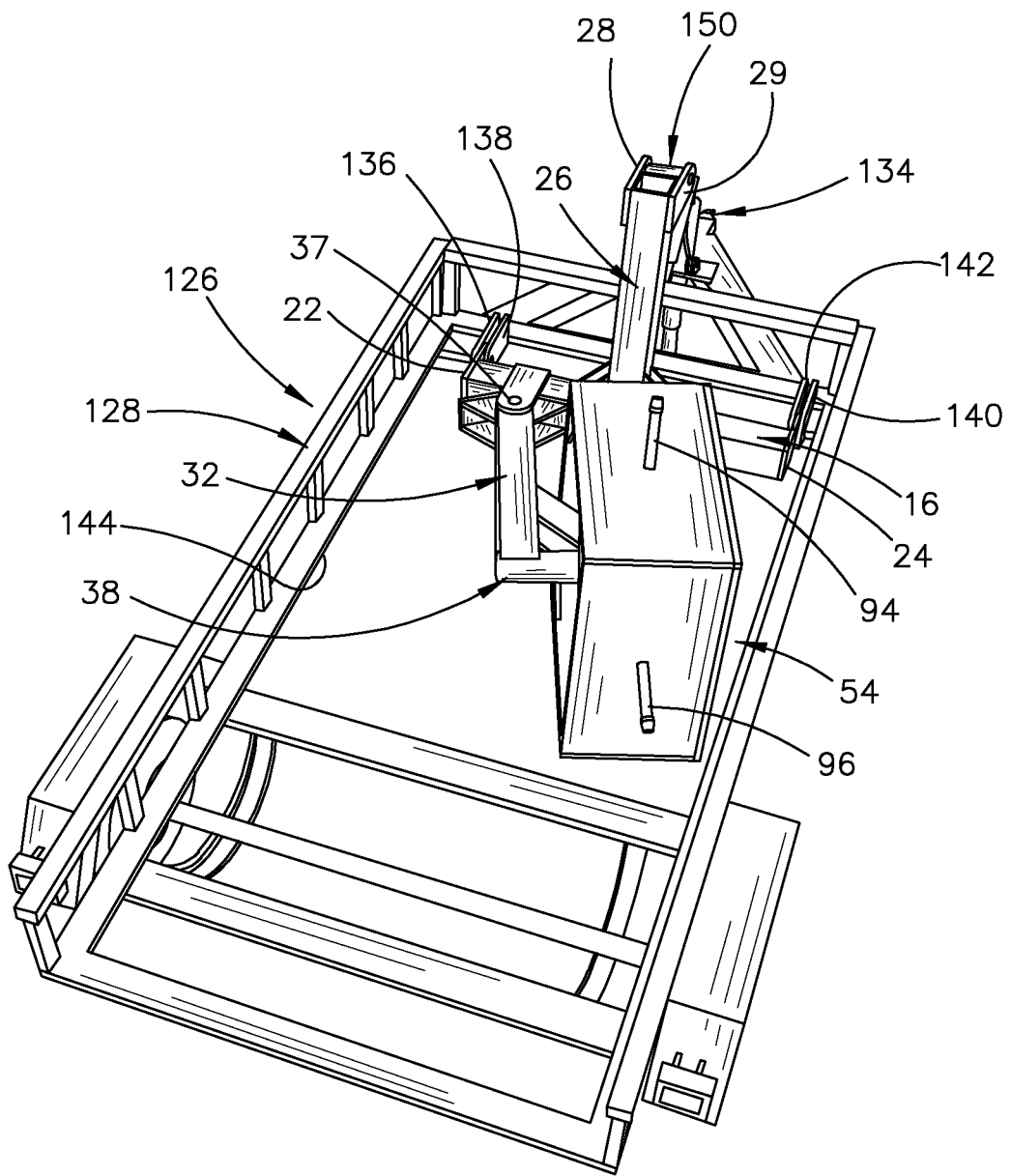
FIG. 16 is an upper rear perspective view of the rolling soil probe assembly mounted on the trailer of FIG. 15.

The rolling soil probe of this invention is designated by the reference numeral 10. The rolling soil probe 10 of this invention is pulled behind a tractor 12 or a truck 13, etc. The rolling soil probe may also be mounted on a trailer as seen in FIGS. 15 and 16. The drawings illustrate a 3-point hitch 14 which is one form of the hitch at the forward end of the rolling soil probe 10. The hitch could be a drawbar hitch, etc. The hitch will be secured to the tractor, truck, etc. It is preferred that the tractor, truck, etc., has means associated therewith to enable the rolling soil probe 10 to be raised from ground engagement to enable the rolling soil probe 10 to be moved from one location to another.

The 3-point drawbar 14 which is shown in FIGS. 1-6 and 9-13 is designed to be attached to the conventional 3-point hitch 15 at the rear end of the tractor 12. The 3-point hitch 15 of the tractor 12 is vertically movable by means of one or more hydraulic cylinders in conventional fashion. The 3-point drawbar 14 includes a horizontally disposed and elongated first frame member 16 having ends 18 and 20 which have hitch plates 22 and 24 secured thereto respectively which extend forwardly therefrom. Drawbar 14 includes a vertically disposed frame member 26 having the lower end thereof secured to the center of frame member 16 and which extends upwardly therefrom. Hitch plates 28 and 29 extend forwardly from the upper end of frame member 26. The 3-point drawbar 14 is secured to the vehicle 3-point hitch where the 3-point drawbar 14 may be raised and lowered with respect to the ground and tractor or the like.

A rearwardly extending mounting bracket 30 is secured to frame member 16 at end 18 thereof. A horizontally disposed and elongated frame member 32, having a forward end 34 and a rearward end 36, has its forward end 34 pivotally secured, about a vertical axis, to mounting bracket 30 by pivot pin 37. The pivotal movement of frame member 32, with respect to frame member 16, is limited by the pair of angle members 32' and 32" secured to the forward end 34 of frame member 32. The numeral 38 refers to a horizontally disposed tubular support having an inner end 40 and an outer end 42. The inner end 40 of tubular support 38 is welded to the rearward end 36 of frame member 32 so as to extend transversely and horizontally from frame member 32. The numeral 44 refers to a conventional spindle and hub assembly. Assembly 44 includes a horizontally disposed spindle or stub axle 46 and hub 48. The inner end of spindle 46 is inserted into the outer end of tubular support 38 and is welded or pinned thereto. The hub 48 is rotatably mounted on the outer end of spindle 46 in conventional fashion and includes a rotatable disc-shaped mounting plate 50 having a plurality of radially spaced-apart bolt openings formed therein. A square wheel 54 is mounted on the mounting plate 50. Square wheel 54 includes a vertically disposed square plate 56 having edges 58, 60, 62 and 64. Plate 56 has a central opening 66 formed therein which receives the outer end of hub 48. Plate 56 has a plurality of radially spaced-apart bolt openings 68 formed therein which register with the bolt openings 52 in mounting plate 50. Bolts 70 extend through the bolt openings 68 and 52 with nuts being secured thereto to secure plate 56 to hub 48. In some cases, the mounting plate 50 will have stud bolts secured thereto which will be received by the bolt openings in plate 56.

Rectangular plates 74, 76, 78 and 80 have their inner edges secured to edges 58, 60, 62 and 64 of plate 56, respectively by welding or the like, and extend transversely from plate 56. The ends of the plates 74, 76, 78 and 80 are secured to the ends of adjacent plates by welding or the like. Gussets 82 are employed as seen in the drawings to strengthen the square wheel 54. As seen, the square plate 56 and the plates 74, 76, 78 and 80 define four corners.

An elongated support plate 84 is secured to the tubular support 38 by braces 86 and 88 for selectively removably supporting a container 90 thereon. The forward end of brace 88 is welded to tubular support 38. The container 90 has an open upper end 91. Container 90 has a short discharge tube 92 which extends from the upper end of container 90.

Elongated and hollow soil probes 94, 96, 98 and 100 are secured to plates 74, 76, 78 and 80 respectively by any conventional means such as welding or the like. Inasmuch as the soil probes 94, 96, 98 and 100 are identical, only a single probe 94 will be described in detail. Probe 94 includes an elongated and hollow body portion 102 having an inner end 104 and an outer end 106. The inner end of body portion 102 communicates with the interior of the square wheel 54. The outer end of the body portion 102 of probe 94 has a truncated conical-shaped tip 108 mounted therein which has an open inner end 110 and an open outer end 112. As seen, the open outer end 112 of tip 108 has a smaller diameter than the open inner end 110 whereby soil samples 113 being driven into the tip 108 will have a diameter which is less than the inside diameter of body portion 102.

Figure 14:
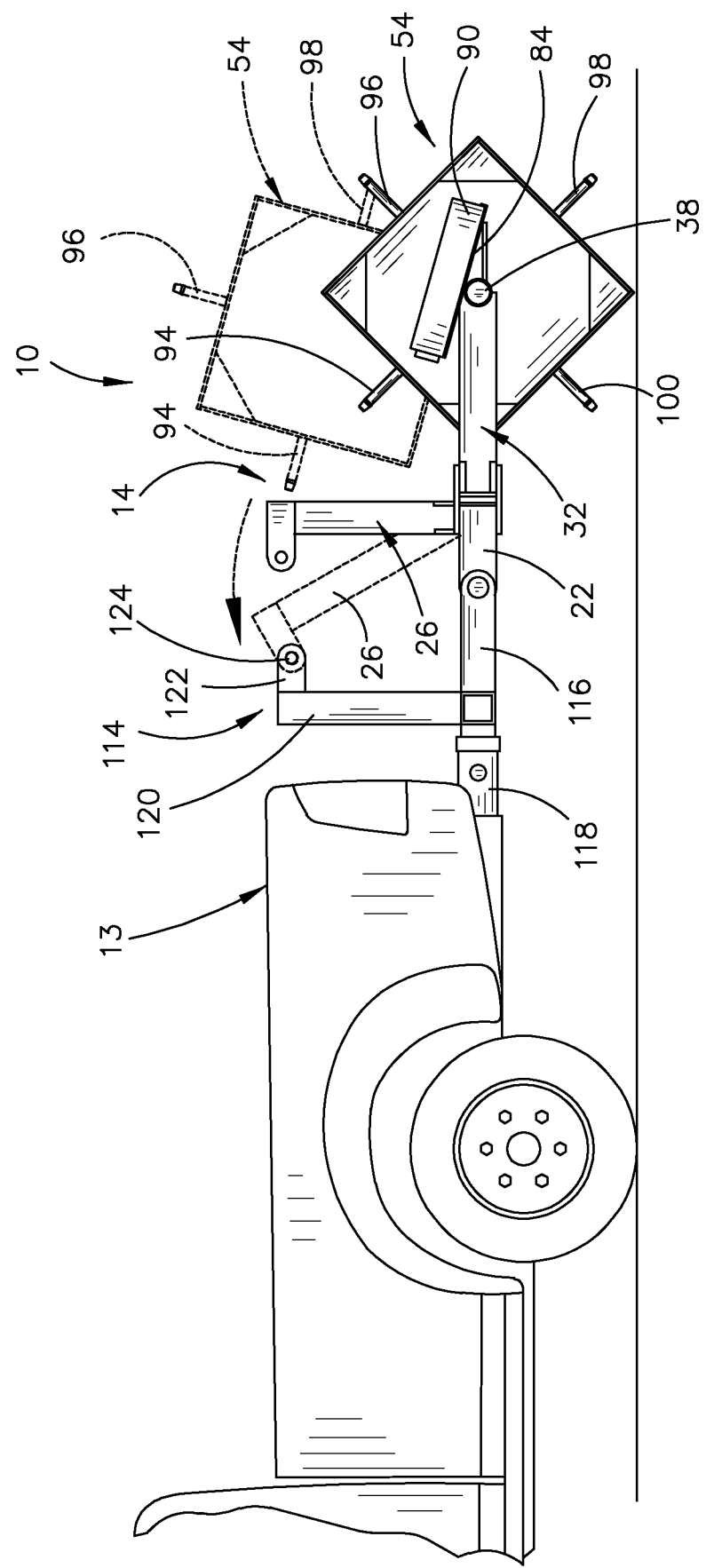
FIG. 14 is a side elevational view illustrating the rolling soil probe assembly being secured to the rear end of a truck.

Referring now to FIG. 14, the truck 13 has a 3-point hitch 114 fixed to the rear end thereof. The 3-point hitch 114 includes a pair of horizontally disposed and horizontally spaced-apart frame members 116 which extend rearwardly from the tubular receiver 118 which is fixed to the frame of the truck 13. A vertically disposed post 120 extends upwardly from the receiver 118 and has a clevis or plate 122 fixed to the upper end thereof. The 3-point hitch 114 is not vertically movable as is the 3-point hitch 15 or the tractor 12.

Figure 1:
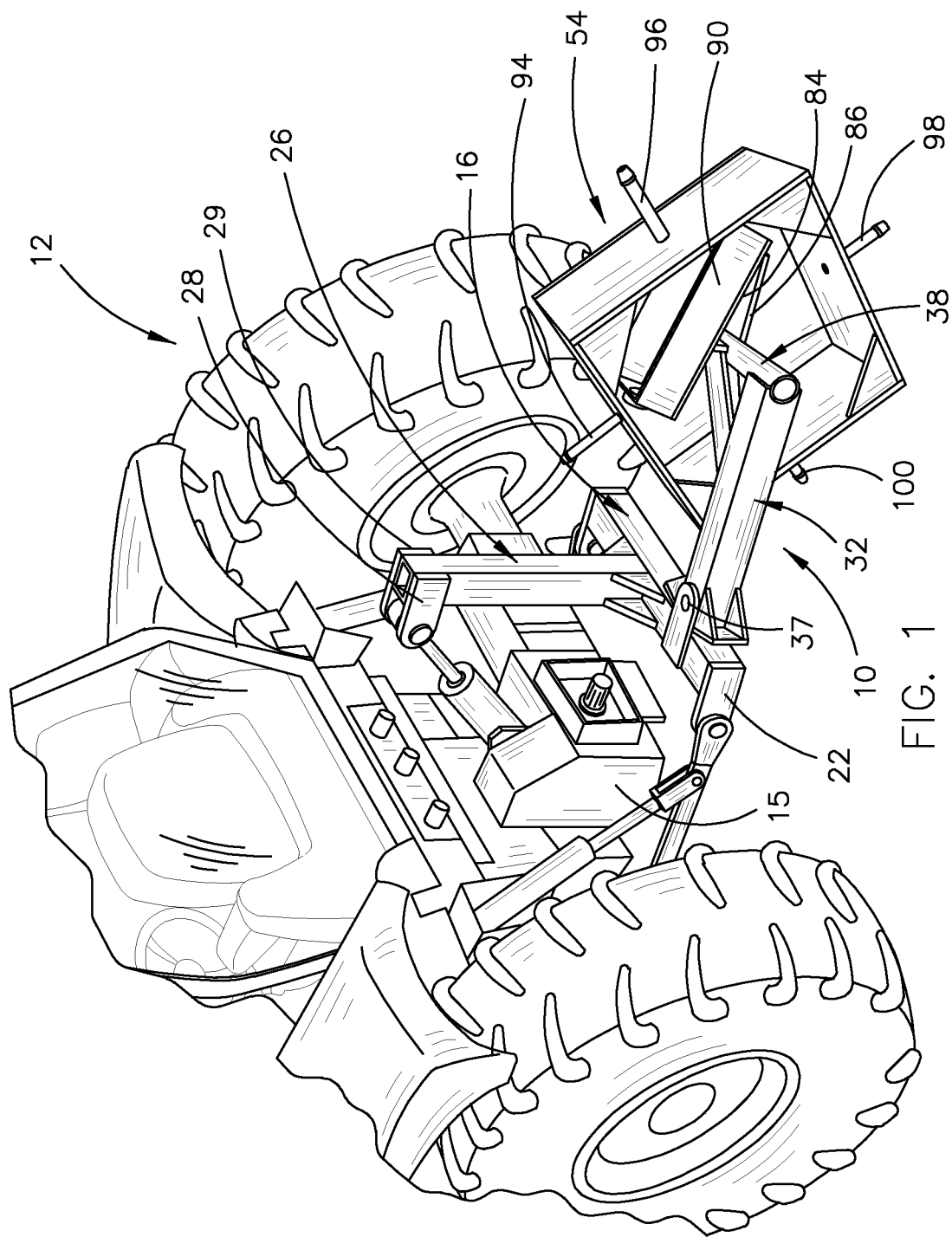
FIG. 1 is a rear perspective view of the rolling soil probe assembly of this invention mounted on the rear end of a tractor.
Figure 2:
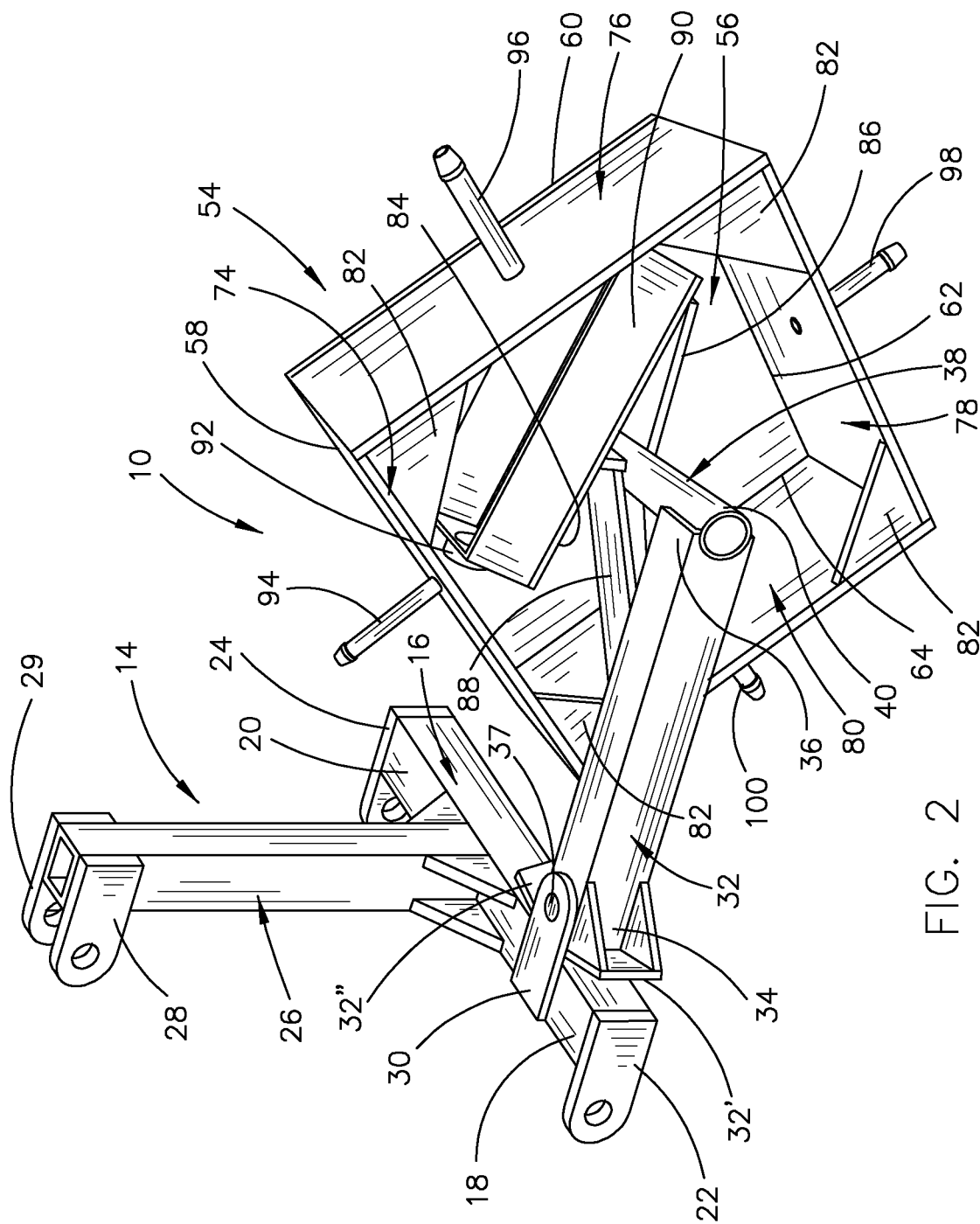
FIG. 2 is a perspective view of the rolling soil probe assembly of this invention.
Figure 3:
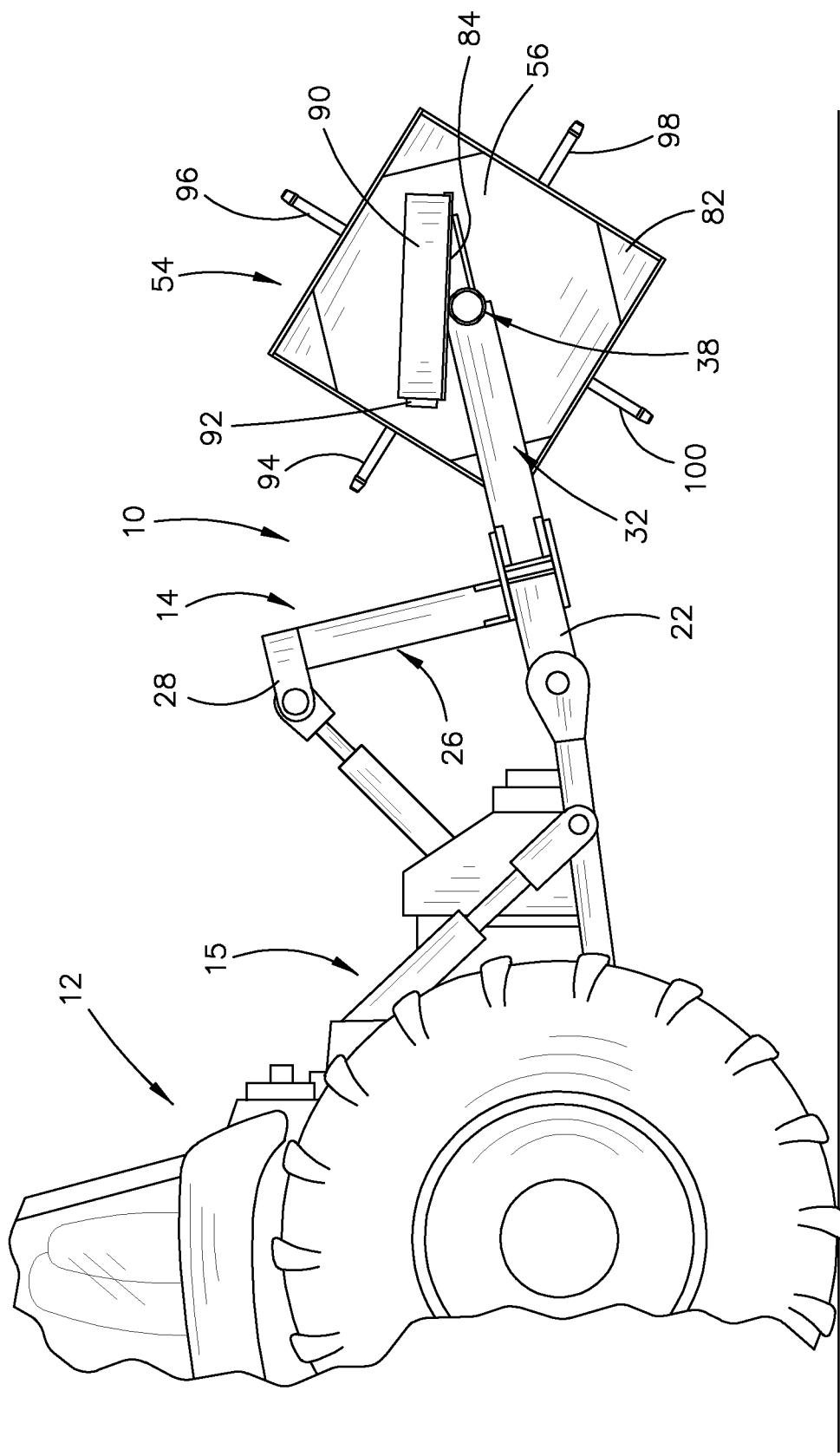
FIG. 3 is a side view of the rolling soil probe assembly mounted on the rear end of a tractor with the rolling soil probe assembly being in an elevated position.
Figure 4:
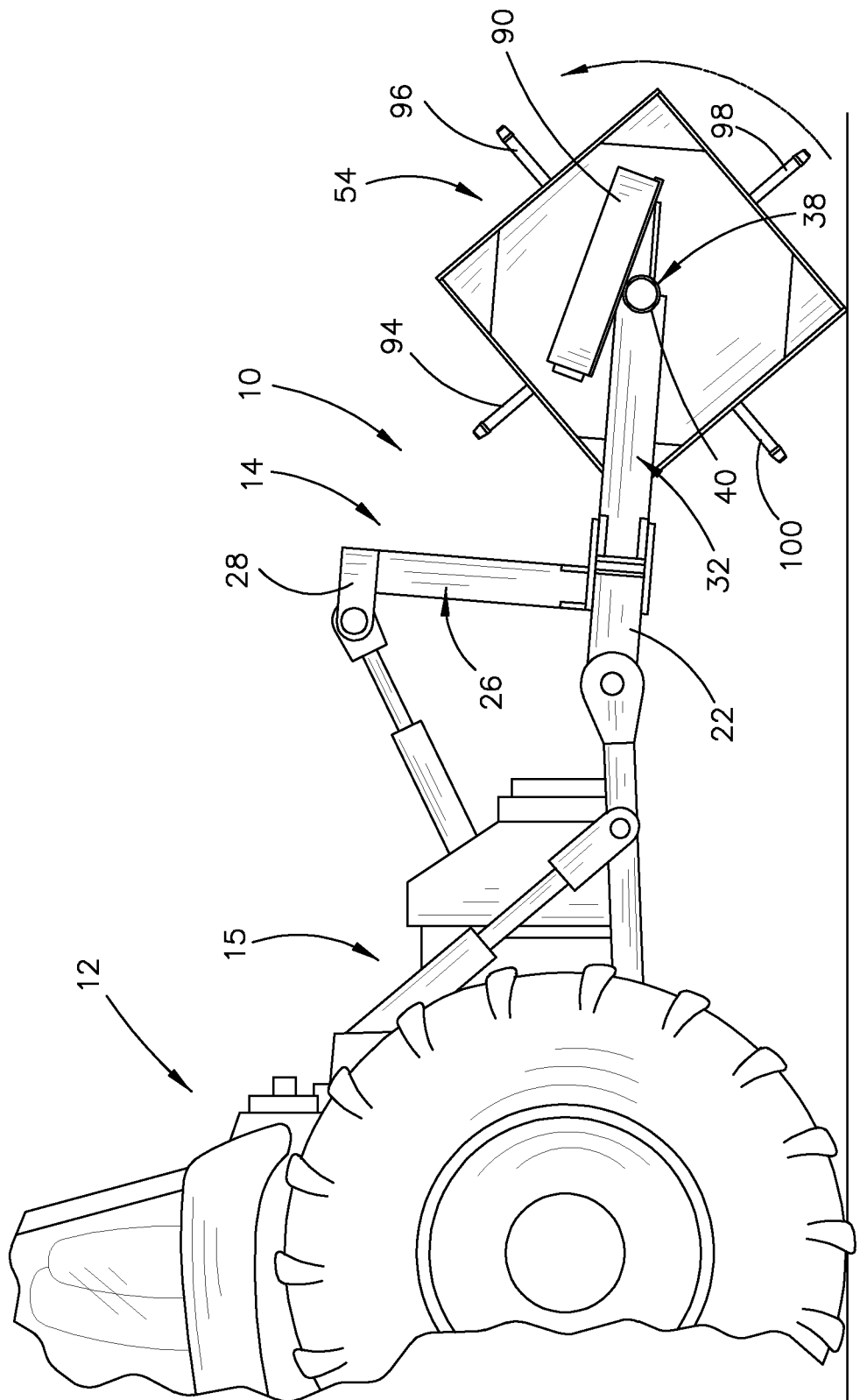
FIG. 4 is a side view of the rolling soil probe assembly mounted on the rear end of a tractor with the rolling soil probe assembly being in a soil engaging position.

The hitch plates 24 and 22 of the drawbar 14 are pivotally secured, about a horizontal axis, to the rear ends of frame members 116 of hitch 114 in the same manner as the hitch plates 24 and 22 are pivotally secured to the 3-point hitch 15 on tractor 12. The pivotal connection of the hitch plates 24 and 22 to the frame members 116 enables the rolling soil probe 10 to be selectively pivotally movable between the solid line position of FIG. 14 to the broken line position of FIG. 14. The rolling soil probe 10 is maintained in the broken line position of FIG. 14 by attaching the hinge plates 28 and 29 of frame member 26 to the clevis 122 by bolt 124 to permit the rolling soil probe 10 to be transported from one location to another location in a raised non-ground engaging position as seen in the broken line position of FIG. 14. When the bolt 124 is removed, the rolling soil probe 10 is manually lowered to the ground engaging position of FIG. 14. In that position, the rolling soil probe will engage the ground by the weight of the rolling soil probe 10. In other words, there is no downward pressure, other than the weight of the rolling soil probe, on the rolling soil probe 10. That is also true for the embodiment of FIGS. 1-13. In operation, when it is desired to obtain soil samples from a field or the like, the rolling soil probe 10 is lowered until the rolling soil probe 10 rests upon the ground. The rolling soil probe 10 will normally be initially positioned on the ground with one of the corners thereof being in engagement with the ground such as seen in FIG. 4. The 3-point hitch 15 will permit the rolling soil probe 10 to freely float on the ground since the 3-point hitch 15 will not be exerting any downward pressure on the rolling soil probe 10. The weight of the rolling soil probe 10 will maintain the rolling soil probe on the ground.

Figure 5:
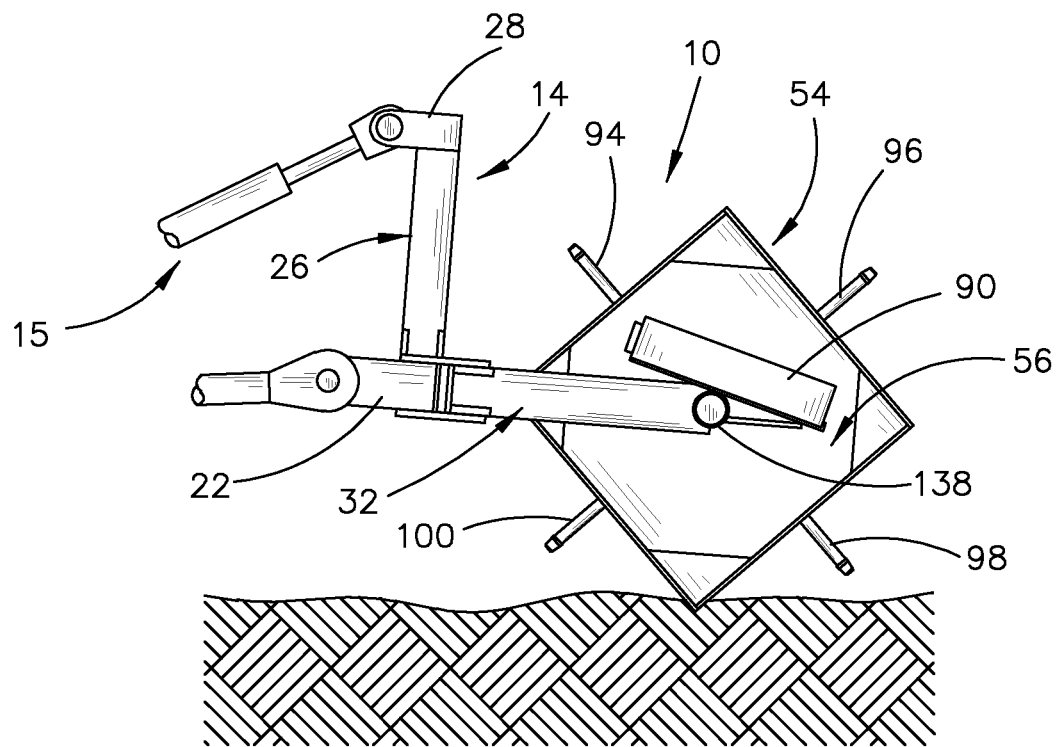
FIG. 5 is a side view similar to FIG. 4 except that the soil being sampled is shown in section.
Figure 6:
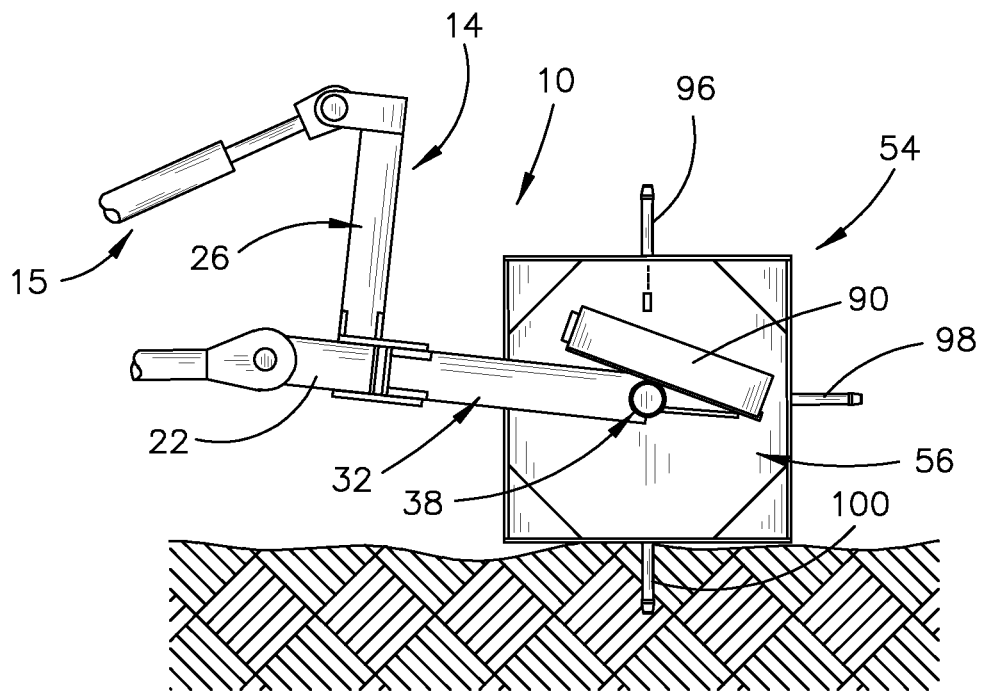
FIG. 6 is a side view similar to FIG. 5 except that the square wheel of the assembly has been rotated from the position of FIG. 5 to the position of FIG. 6 and with one side of the square wheel being positioned on the soil and with one soil probe being inserted into the ground.
Figure 8:
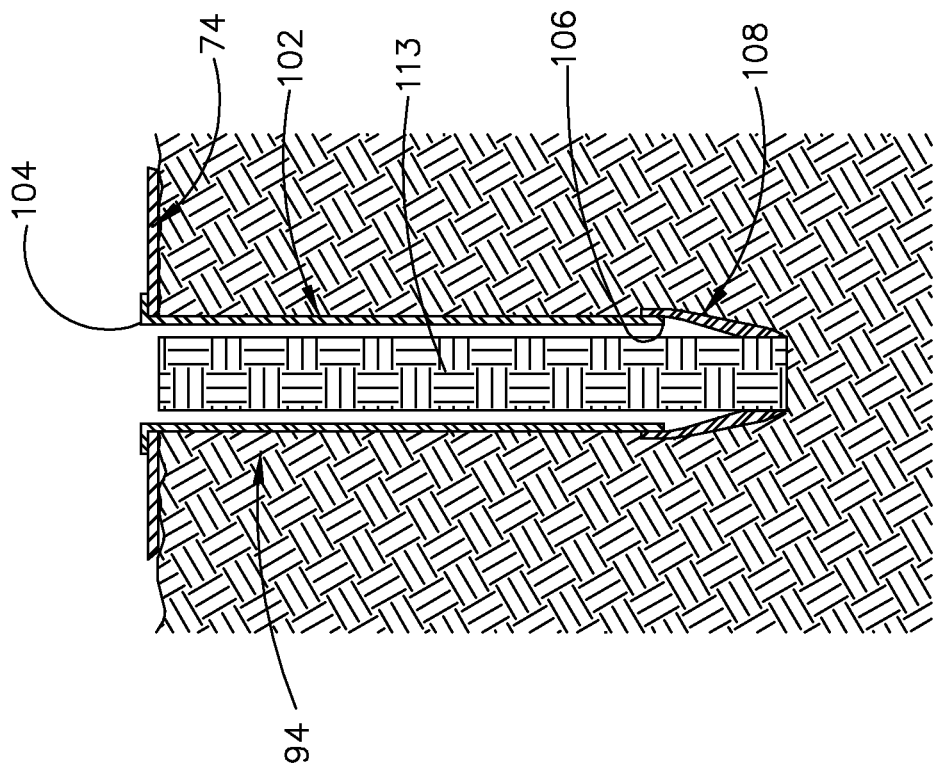
FIG. 8 is a sectional view illustrating a soil probe inserted into the soil and which illustrates a soil sample within the soil probe.
Figure 7:
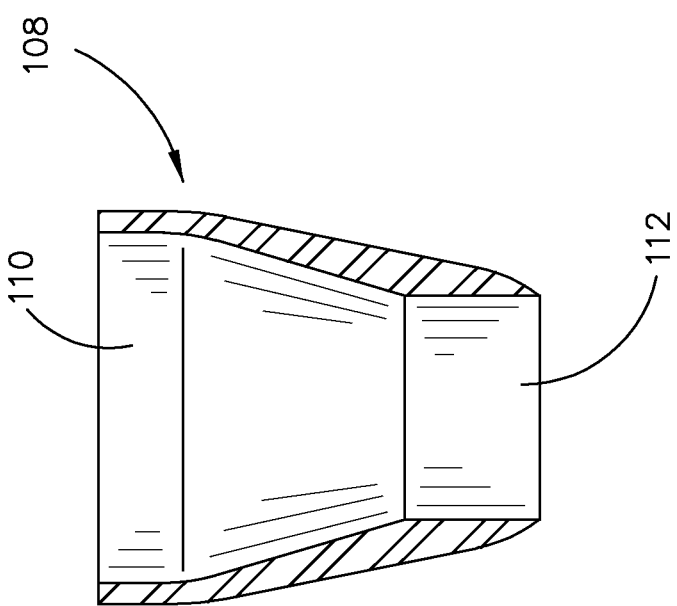
FIG. 7 is a sectional view of the tip of one of the soil probes.
Figure 9:
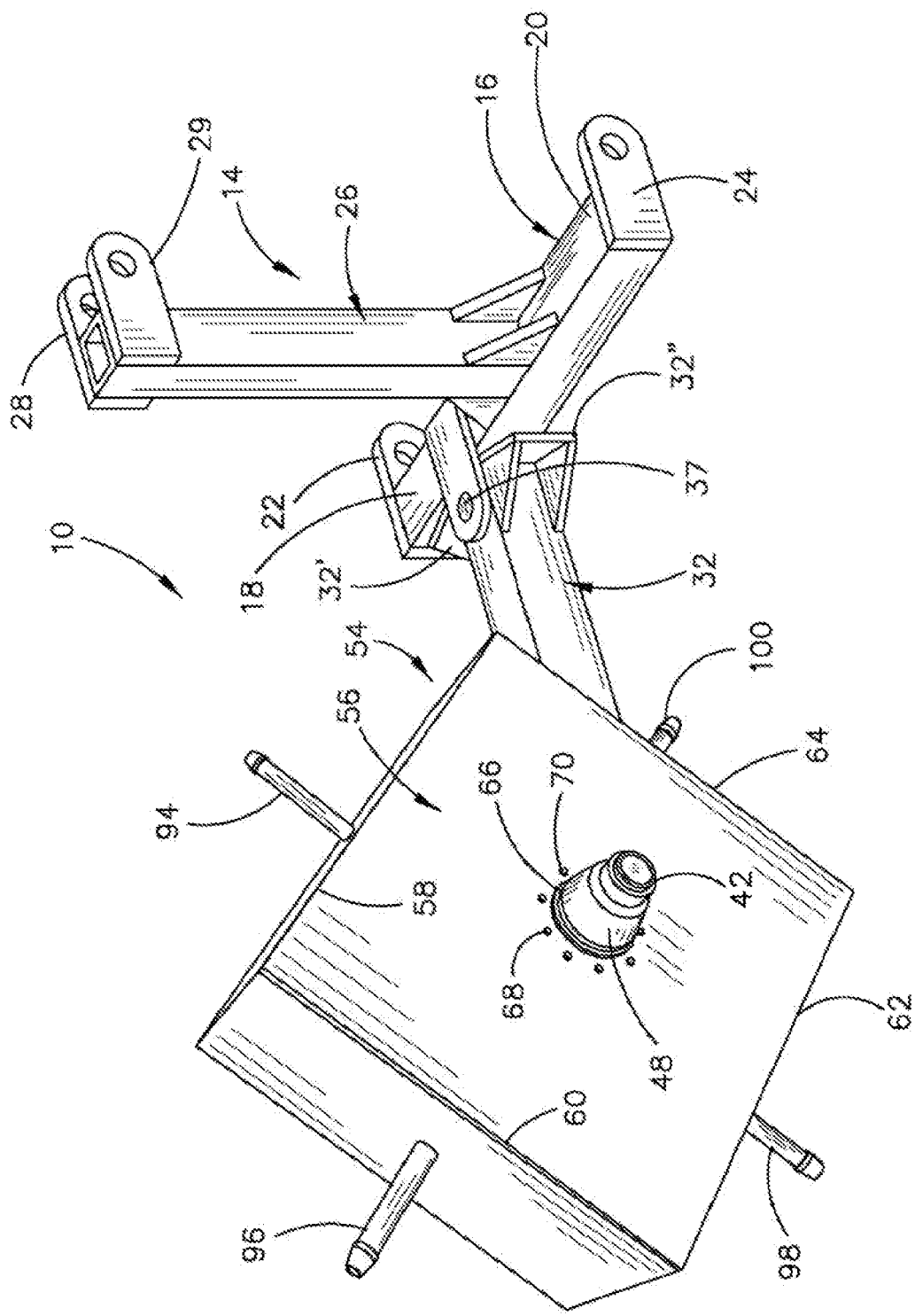
FIG. 9 is a perspective view of the rolling soil probe assembly as seen from the right side thereof.
Figure 10:
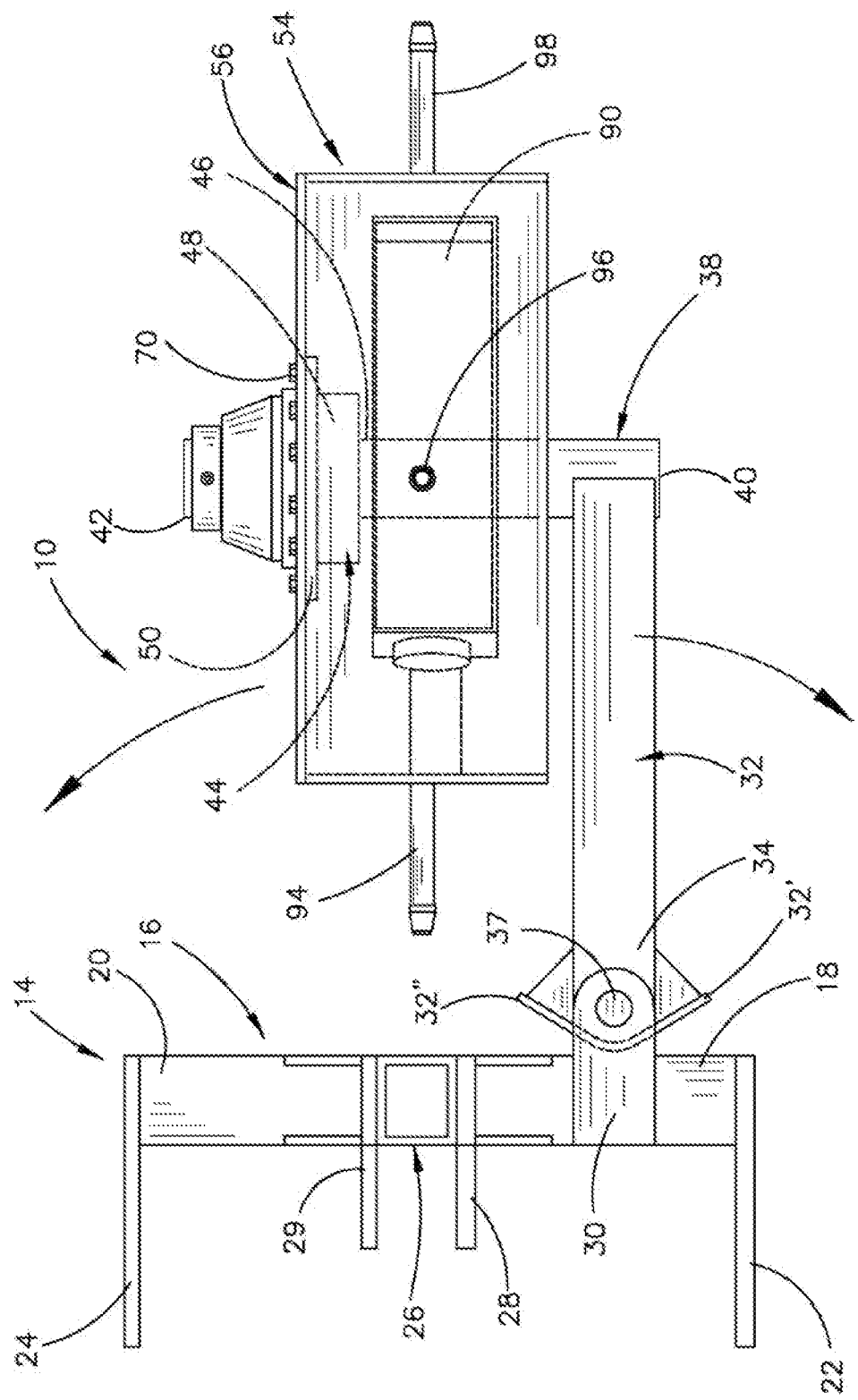
FIG. 10 is a top elevational view of the rolling soil probe assembly.
Figure 11:
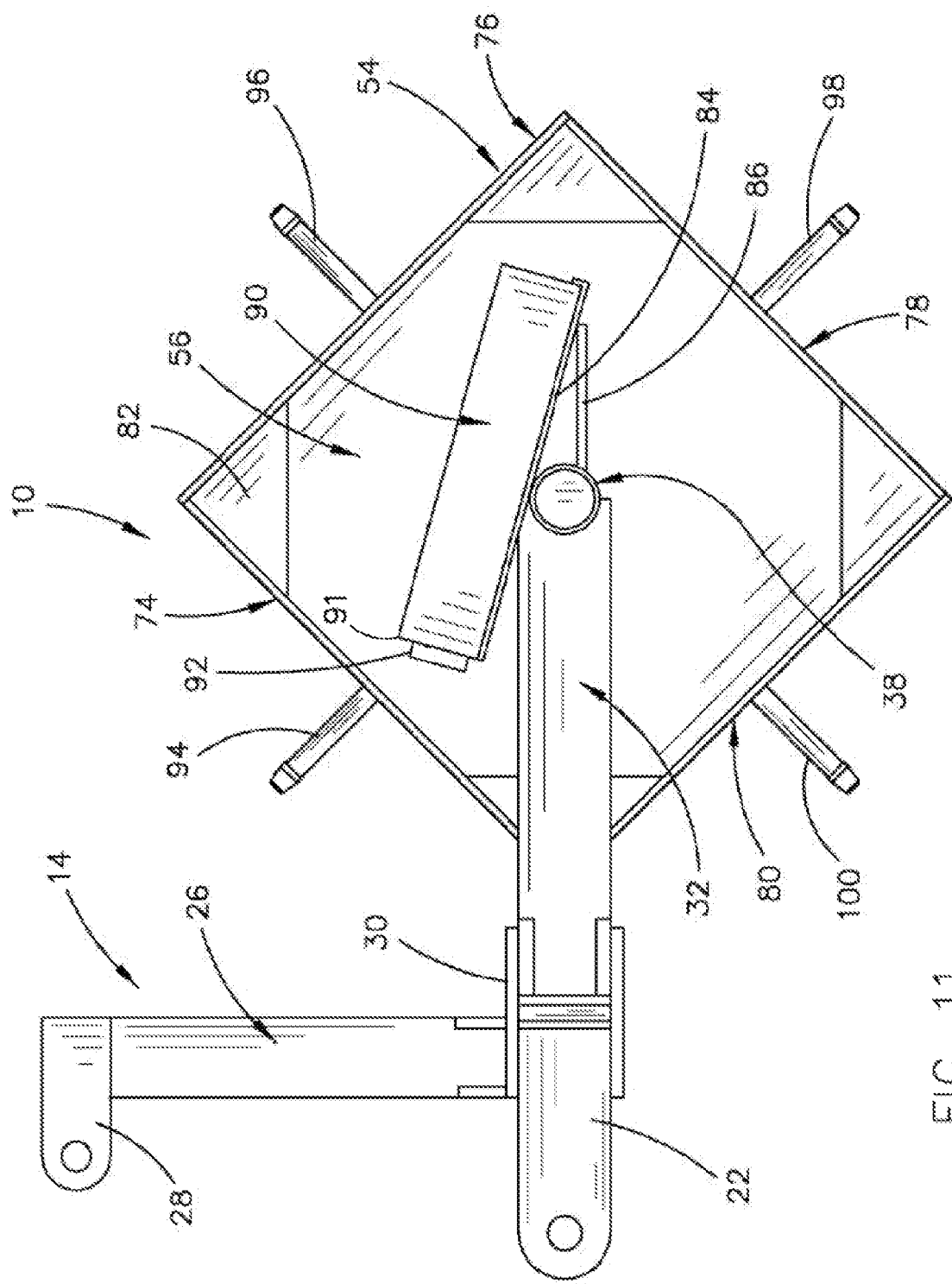
FIG. 11 is a left side view of the rolling soil probe assembly.
Figure 12:
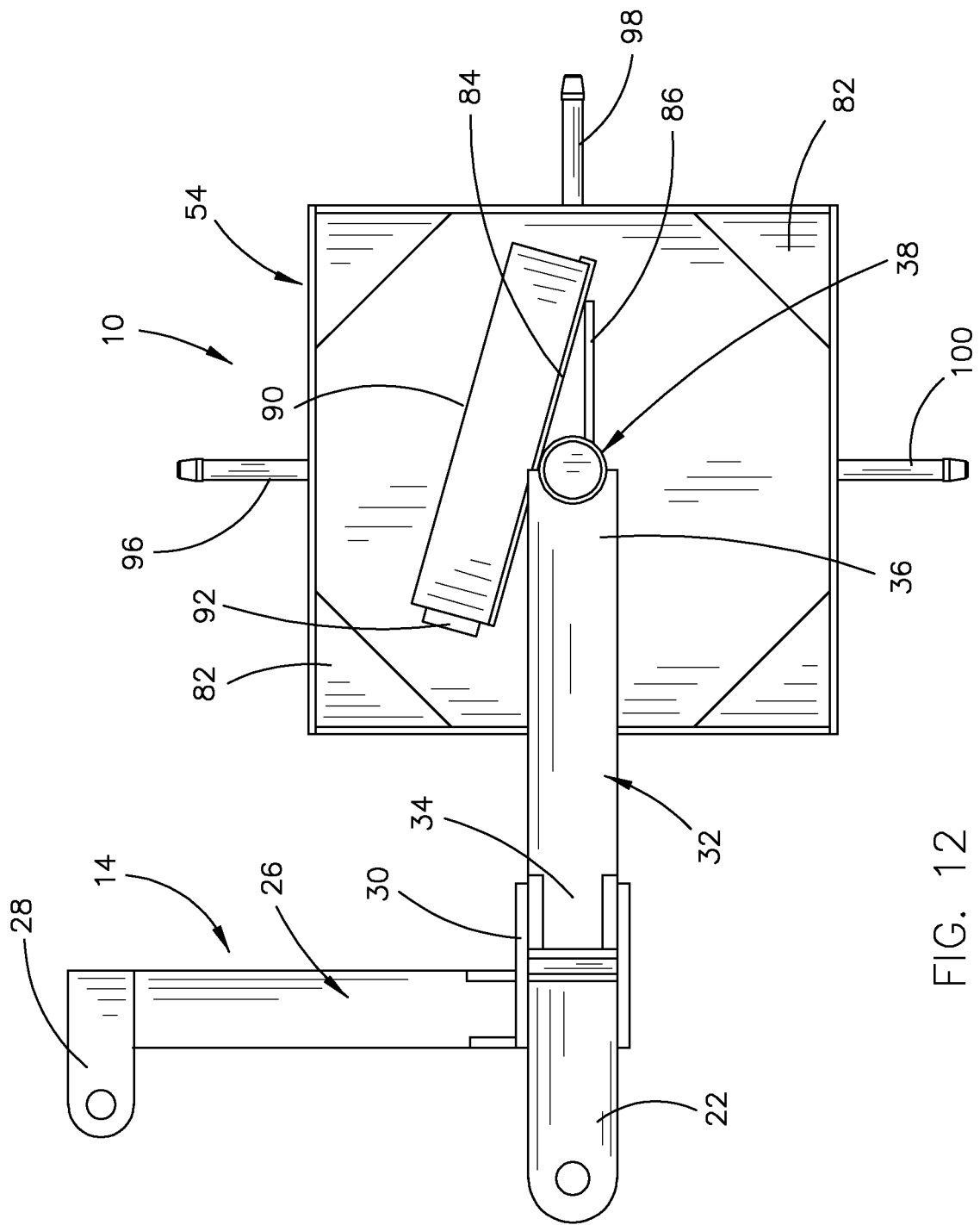
FIG. 12 is a left side view of the rolling soil probe assembly and which has been rotated 45 degrees from FIG. 11.
Figure 13:
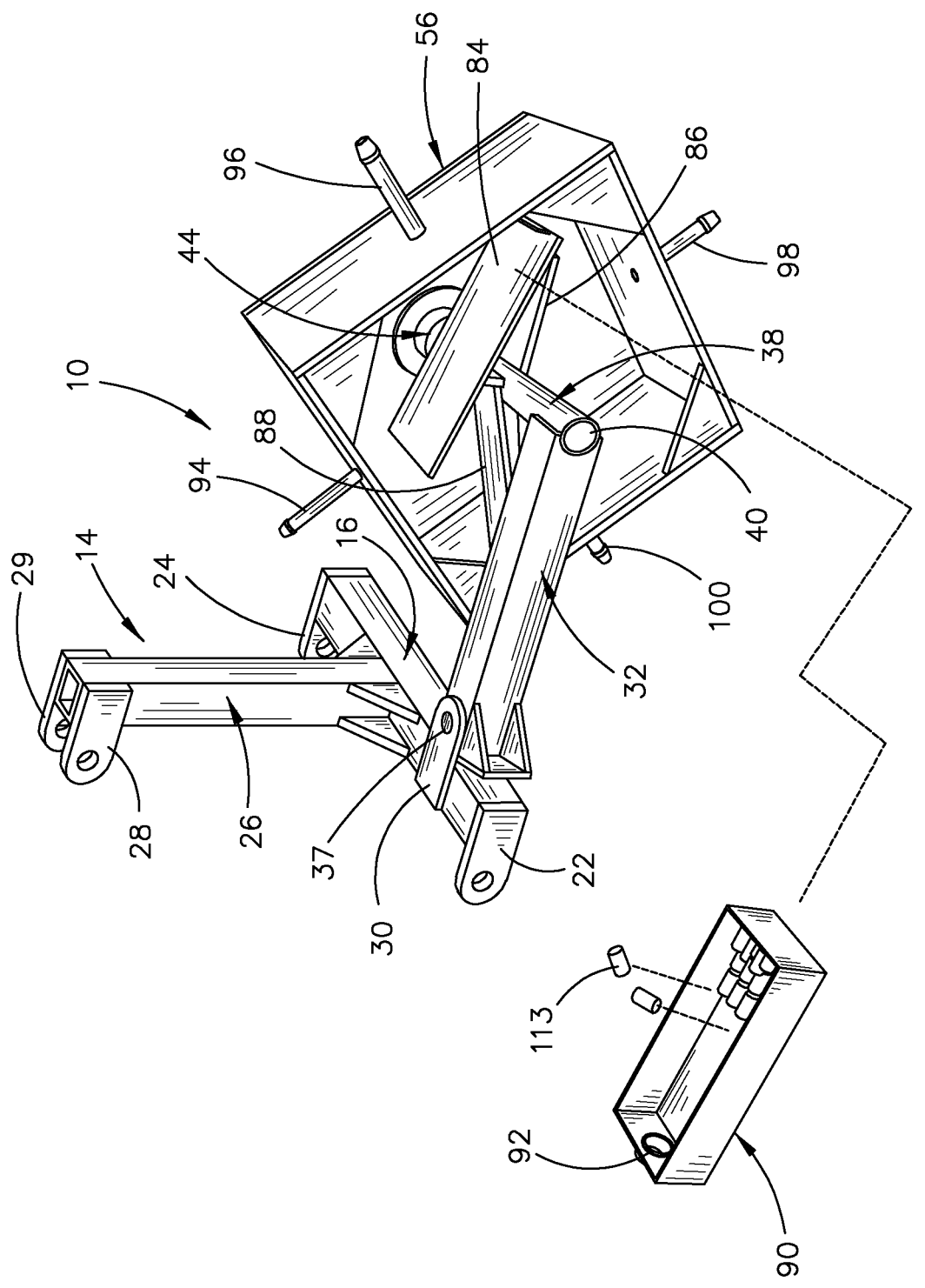
FIG. 13 is an exploded perspective view of the rolling soil probe assembly and which illustrates the soil sample container having been removed from the square wheel thereof.

Assuming that the rolling soil probe 10 is in the position of FIGS. 4 and 5, the tractor 12 will be driven forwardly. The protruding corners of the rolling soil probe 10 provide a lifting and dropping action to assist in pushing and pulling the soil probe into and out of the ground and dropping the soil cores into the sample collection container 90. There is a "slamming" effect when the rolling soil probe 10 is called to one of the flat sides of the square wheel 54 which not only drives the soil probe 10 into the ground but which also dislodges the soil sample from the uppermost probe which falls into the collection containers 90. Gravity, slamming effect and the smaller diameter probe tip 108 removes the soil sample from within the probe.

The pivotal connection of frame member 32 with respect to frame member 18 about a pivot pin 37 enables the rolling soil probe 10 to be pulled in a circle around a desired sample point. In summary somewhat, there is only one soil probe 10 in engagement with the ground at one time which is due to the square wheel 54. The soil probes of this invention also penetrate the ground at a steeper angle than is possible in the round wheel sampler devices.

FIGS. 15 and 16 illustrate another way of mounting the rolling soil probe 10 onto a wheeled vehicle such as a trailer 126. Trailer 126 includes a frame 128 which is supported by wheels 130 and 132. Frame 128 has a ball hitch 134 assembly at the forward end thereof for attachment to a vehicle having a ball hitch at the rearward end thereof in conventional fashion. A pair of spaced-apart support plates 136 and 138 are secured to frame 128 at one side thereof and a pair of spaced-apart plates 140 and 142 are secured to frame 128 and the other side thereof.

The rolling soil probe 10 is positioned in the opening 144 of frame 128 of trailer 126 as illustrated in FIG. 16. Hitch plate 22 of rolling soil probe 10 is positioned between support plates 136 and 138 and pivotally secured thereto by pivot pin 146. Hitch plate 24 of rolling soil probe 10 is positioned between the support plates 140 and 142 and pinned thereto. Thus, the forward end of the rolling soil probe 10 is pivotally secured to frame 128 so as to be movable between the upper and lower positions with respect to the trailer 126. The apparatus for pivotally moving the rolling soil probe 10 between upper and lower positions will now be described. A flexible cable 148 has its rearward end secured to the upper end of frame member 26 by pin 150. The forward end of cable 148 is fixed to hitch 134 at 152.

The numeral 154 refers to an electric linear actuator of conventional design. The base 156 of actuator 154 is secured to frame 128 at 158. The hitch 134 is preferably supported by a vertically movable jack 160 of conventional design when the trailer 126 is not being towed. Thus, when the actuator 154 is extended, the cable 148 becomes taut and pulls the rolling soil probe 10 to the upper position. When the actuator 154 is retracted, the rolling soil probe 10 is allowed to pivotally move downwardly so that the square wheel 54 is in contact with the ground so that the square wheel 54 will roll as the trailer 126 is towed forwardly. The functioning of the rolling soil probe 10 of FIGS. 15 and 16 is the same as previously described.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A rolling soil probe assembly, comprising:
   an elongated and horizontally disposed frame member having a forward end and a rearward end, the forward end of the frame member coupled to a drawbar so as to extend rearwardly therefrom;
   an elongated and horizontally disposed support member having an inner end and an outer end, the inner end of the support member coupled to the rearward end of the frame member so as to extend transversely therefrom;
   a horizontally disposed spindle and hub assembly having a spindle with an inner end and outer end and a hub coupled to the outer end of the spindle, the hub configured to rotate with respect to the spindle, the inner end of the spindle coupled to the outer end of the support member whereby the spindle extends outwardly from the outer end of the support member;
   a wheel including:
      a vertically disposed plate coupled to the hub, the plate having a plurality of edges,
      a plurality of rectangular plates each having a first end, a second end, an inner end, and an outer end, the outer end of each rectangular plate coupled to a corresponding edge among the plurality of edges of the vertically disposed plate, the first end of each rectangular plate coupled to a second end of a first adjacent rectangular plate and the second end of each rectangular plate coupled to a first end of a second adjacent rectangular plate, each rectangular plate including a probe opening, and
      a plurality of elongated soil probes corresponding to the plurality of rectangular plates, each soil probe configured to receive a soil sample via an open upper end and configured to drop the soil sample via an open lower end; and
   a soil sample collection container coupled to the support member, the soil sample collection container located between the first and second ends of the plurality of rectangular plates, the soil sample collection container configured to receive a soil sample dropped from each soil probe among the plurality of soil probes.

2. The assembly of claim 1, further comprising a 3-point drawbar configured to couple to a 3-point hitch of a vehicle, the 3-point drawbar having a forward side and a rearward side.

3. The assembly of claim 2, wherein the frame member is pivotably coupled to the 3-point drawbar, the frame member configured to pivot about a vertical axis relative to the 3-point drawbar.

4. The assembly of claim 3, wherein the frame member further includes a set of angle members coupled proximately to the forward end of the frame member, the set of angle members configured to limit pivotal movement of the frame member relative to the 3-point drawbar.

5. The assembly of claim 2, wherein the 3-point drawbar is pivotably coupled to the 3-point hitch.

6. The assembly of claim 1, wherein each soil probe further comprises:
an elongated hollow body portion with an open upper end and an open lower end, the open lower end coupled to a corresponding rectangular plate among the plurality of rectangular plates, the upper end in communication with the probe opening of the corresponding rectangular plate; and
a hollow probe tip having an open upper end and an open lower end, the upper end of the probe in communication with the upper end of the elongated body portion.

7. The assembly of claim 6, wherein the open end of the probe tip has an inside diameter that is less than the inside diameter of the body portion.

8. The assembly of claim 6, wherein the hollow probe tip has a truncated conical-shaped tip.

9. The assembly of claim 1, further comprising one or more support plates coupled to the support member, the soil sample collection container configured to selectively couple to the one or more support plates.

10. The assembly of claim 1, wherein the soil sample collection container further comprises a discharge tube.

11. The assembly of claim 1, further comprising a plurality of gussets, wherein each gusset is coupled to a first rectangular plate and a second adjacent rectangular plate among the plurality of rectangular plates.

12. A rolling soil probe assembly, comprising:
an elongated and horizontally disposed frame member having a forward end and a rearward end, the forward end of the frame member coupled to a drawbar so as to extend rearwardly therefrom;
an elongated and horizontally disposed support member having an inner end and an outer end, the inner end of the support member coupled to the rearward end of the frame member so as to extend transversely therefrom;
a horizontally disposed spindle and hub assembly having a spindle with an inner end and outer end and a hub coupled to the outer end of the spindle, the hub configured to rotate with respect to the spindle, the inner end of the spindle coupled to the outer end of the support member whereby the spindle extends outwardly from the outer end of the support member;
a wheel including:
a vertically disposed plate having four edges, the plate having a plurality of edges,
a set of four rectangular plates each having a first end, a second end, an inner end, and an outer end, the outer end of each rectangular plate coupled to a corresponding edge among the four edges of the vertically disposed plate, the first end of each rectangular plate coupled to a second end of a first adjacent rectangular plate and the second end of each rectangular plate coupled to a first end of a second adjacent rectangular plate, each rectangular plate including a probe opening, and
a set of four elongated soil probes corresponding to the set of four rectangular plates, each soil probe configured to receive a soil sample via an open upper end and configured to drop the soil sample via an open lower end; and
a soil sample collection container coupled to the support member, the soil sample collection container located between the first and second ends of the set of four rectangular plates, the soil sample collection container configured to receive a soil sample dropped from each soil probe among the set of four soil probes.

13. The assembly of claim 12, further comprising a 3-point drawbar configured to couple to a 3-point hitch of a vehicle, the 3-point drawbar having a forward side and a rearward side.

14. The assembly of claim 13, wherein the 3-point drawbar is pivotably coupled to the 3-point hitch.

15. The assembly of claim 13, wherein the frame member is pivotably coupled to the 3-point drawbar, the frame member configured to pivot about a vertical axis relative to the 3-point drawbar.

16. The assembly of claim 15, wherein the frame member further includes a set of angle members coupled proximately to the forward end of the frame member, the set of angle members configured to limit pivotal movement of the frame member relative to the 3-point drawbar.

17. The assembly of claim 12, wherein each soil probe further comprises:
an elongated hollow body portion with an open upper end and an open lower end, the open lower end coupled to a corresponding rectangular plate among the plurality of rectangular plates, the upper end in communication with the probe opening of the corresponding rectangular plate; and
a hollow probe tip having an open upper end and an open lower end, the upper end of the probe in communication with the upper end of the elongated body portion.

18. The assembly of claim 17, wherein the open end of the probe tip has an inside diameter that is less than the inside diameter of the body portion.

19. The assembly of claim 12, further comprising one or more support plates coupled to the support member, the soil sample collection container configured to selectively couple to the one or more support plates.

20. A rolling soil probe assembly, comprising:
a 3-point drawbar configured to couple to a 3-point hitch of a vehicle, the 3-point drawbar having a forward side and a rearward side, the 3-point drawbar configured to pivotably couple to the 3-point hitch;
an elongated and horizontally disposed frame member having a forward end and a rearward end, the forward end of the frame member pivotably coupled to a drawbar so as to extend rearwardly therefrom, the frame member configured to pivot about a vertical axis relative to the 3-point drawbar;
an elongated and horizontally disposed support member having an inner end and an outer end, the inner end of the support member pivotably coupled to the rearward end of the frame member so as to extend transversely therefrom, the frame member including a set of angle members coupled proximately to the forward end of the frame member, the set of angle members configured to limit pivotal movement of the frame member relative to the 3-point drawbar;

a horizontally disposed spindle and hub assembly having a spindle with an inner end and outer end and a hub coupled to the outer end of the spindle, the hub configured to rotate with respect to the spindle, the inner end of the spindle coupled to the outer end of the support member whereby the spindle extends outwardly from the outer end of the support member;

a wheel including:

a vertically disposed plate coupled to the hub, the plate having a plurality of edges, a plurality of rectangular plates each having a first end, a second end, an inner end, and an outer end, the outer end of each rectangular plate coupled to a corresponding edge among the plurality of edges of the vertically disposed plate, the first end of each rectangular plate coupled to a second end of a first adjacent rectangular plate and the second end of each rectangular plate coupled to a first end of a second adjacent rectangular plate, each rectangular plate including a probe opening, and a plurality of elongated soil probes corresponding to the plurality of rectangular plates, each soil probe including:

an elongated hollow body portion with an open upper end and an open lower end, the open lower end coupled to a corresponding rectangular plate among the plurality of rectangular plates, the upper end in communication with the probe opening of the corresponding rectangular plate, a hollow probe tip having an open upper end and an open lower end, the upper end of the probe in communication with the upper end of the elongated body portion, the open end having an inside diameter that is less than the inside diameter of the body portion, the hollow probe tip having a truncated conical-shaped tip, and the probe tip and the body portion configured to receive a soil sample via the open upper end and configured to drop the soil sample via the open lower end; and a soil sample collection container coupled to the support member, the soil sample collection container located between the first and second ends of the plurality of rectangular plates, the soil sample collection container configured to receive a soil sample dropped from each soil probe among the plurality of soil probes, the soil sample collection container having a discharge tube.

\* \* \* \* \*